United States Patent
Gatayama et al.

(10) Patent No.: US 10,863,962 B2
(45) Date of Patent: Dec. 15, 2020

(54) X-RAY COMPUTED TOMOGRAPHY APPARATUS AND CONTRAST MEDIUM INFLOW AMOUNT DETECTION METHOD

(71) Applicant: Toshiba Medical Systems Corporation, Otawara (JP)

(72) Inventors: Kazuki Gatayama, Otawara (JP); Tatsuya Watanabe, Nasushiobara (JP); Katsuhiko Ishida, Nasushiobara (JP); Shinya Kawanabe, Otawara (JP)

(73) Assignee: Canon Medical Systems Corporation, Otawara (JP)

( * ) Notice: Subject to any disclaimer, the term of this patent is extended or adjusted under 35 U.S.C. 154(b) by 990 days.

(21) Appl. No.: 14/976,754

(22) Filed: Dec. 21, 2015

(65) Prior Publication Data

US 2016/0100815 A1 Apr. 14, 2016

Related U.S. Application Data

(63) Continuation of application No. PCT/JP2014/068236, filed on Jul. 8, 2014.

(30) Foreign Application Priority Data

Jul. 8, 2013 (JP) .................................. 2013-142496

(51) Int. Cl.
  *A61B 6/00* (2006.01)
  *A61B 6/03* (2006.01)
  *A61M 5/00* (2006.01)

(52) U.S. Cl.
  CPC .............. *A61B 6/54* (2013.01); *A61B 6/032* (2013.01); *A61B 6/481* (2013.01); *A61B 6/486* (2013.01);
  (Continued)

(58) Field of Classification Search
  CPC ......... A61B 6/032; A61B 6/481; A61B 6/486; A61B 6/488; A61B 6/507; A61B 6/5205;
  (Continued)

(56) References Cited

U.S. PATENT DOCUMENTS 5,987,093 A 11/1999 Ozaki
2003/0108149 A1 6/2003 Tsuyuki
(Continued)

FOREIGN PATENT DOCUMENTS

JP 10-118016 5/1998
JP 10-211198 8/1998
(Continued)

OTHER PUBLICATIONS

International Search Report dated Aug. 5, 2014 in PCT/JP2014/068236, filed Jul. 8, 2014 (with English Translation).
(Continued)

*Primary Examiner* — Mark D Remaly
(74) *Attorney, Agent, or Firm* — Oblon, McClelland, Maier & Neustadt, L.L.P.

(57) ABSTRACT

According to an embodiment, an X-ray computed tomography apparatus includes reconstruction circuitry and control circuitry. The reconstruction circuitry is configured to, at the time of the monitoring scan, based on an output of an X-ray detector for detecting X-rays having passed through the object, reconstruct a first image concerning the object at the time of administration of the contrast medium and a second image concerning the object after a predetermined period elapses since administration of the contrast medium. The control circuitry is configured to shift from the monitoring scan to the actual scan based on a change amount of a CT value obtained when the entire reconstructed first image is compared with the entire reconstructed second image.

3 Claims, 5 Drawing Sheets

(52) U.S. Cl.
CPC .............. *A61B 6/488* (2013.01); *A61B 6/507* (2013.01); *A61B 6/5217* (2013.01); *A61B 6/541* (2013.01); *A61B 6/545* (2013.01); *A61M 5/007* (2013.01); *A61B 6/5205* (2013.01)

(58) Field of Classification Search
CPC ......... A61B 6/5217; A61B 6/54; A61B 6/541; A61B 6/545; A61M 5/007
See application file for complete search history.

(56) References Cited

U.S. PATENT DOCUMENTS

| | | |
|---|---|---|
| 2009/0022268 A1 | 1/2009 | Kudo |
| 2011/0194675 A1 | 8/2011 | Tsuyuki et al. |
| 2012/0243760 A1* | 9/2012 | Manabe ................ G06T 7/0012 382/131 |

FOREIGN PATENT DOCUMENTS

| | | |
|---|---|---|
| JP | 2003-245275 | 9/2003 |
| JP | 2006-175213 | 7/2006 |
| JP | 2007-289297 | 11/2007 |
| JP | 2009-22452 | 2/2009 |
| JP | 2009-28194 | 2/2009 |
| JP | 2011-152187 | 8/2011 |
| JP | 2011-172924 | 9/2011 |

OTHER PUBLICATIONS

Written Opinion dated Aug. 5, 2014 in PCT/JP2014/068236, filed Jul. 8, 2014.

\* cited by examiner

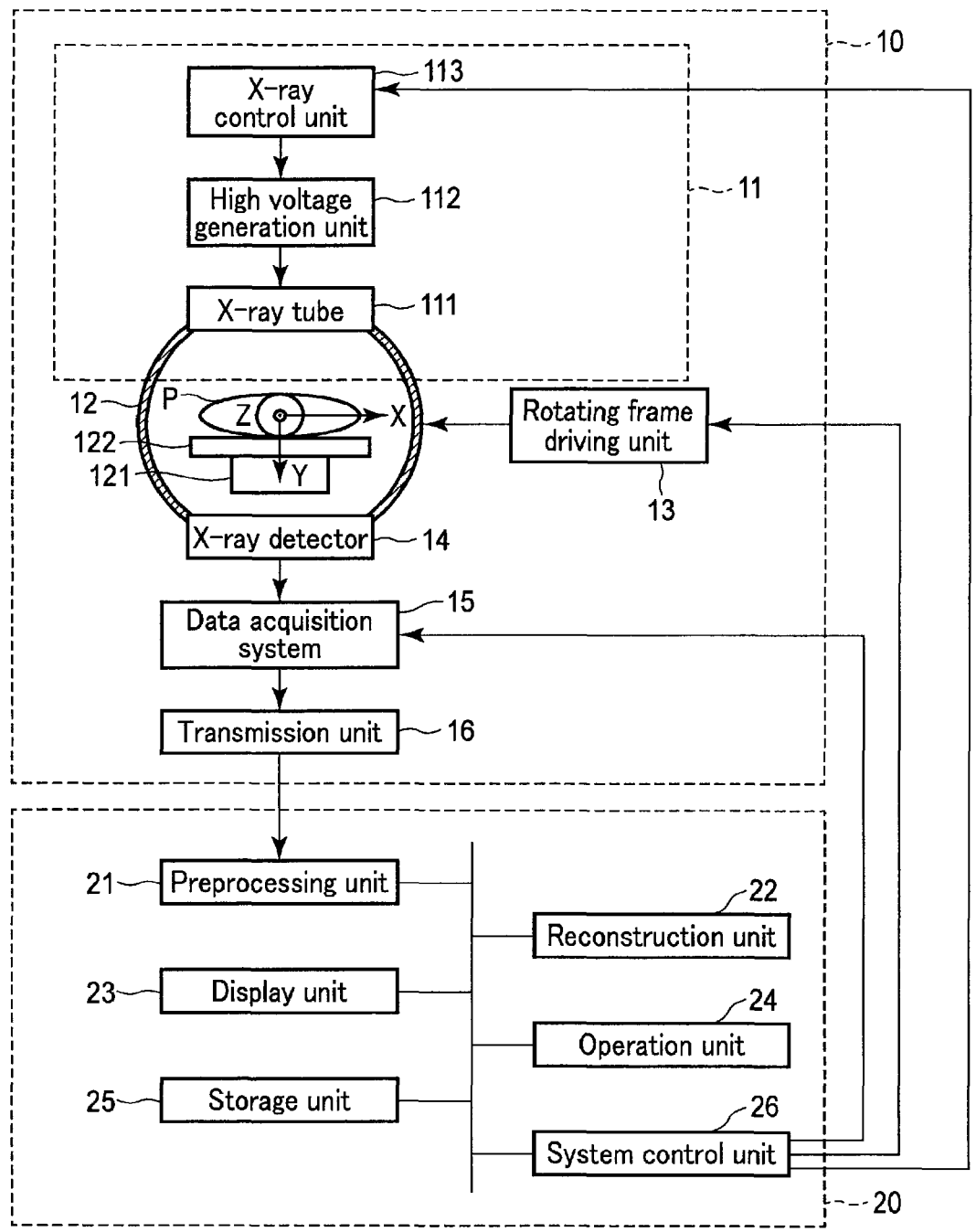
F I G. 1

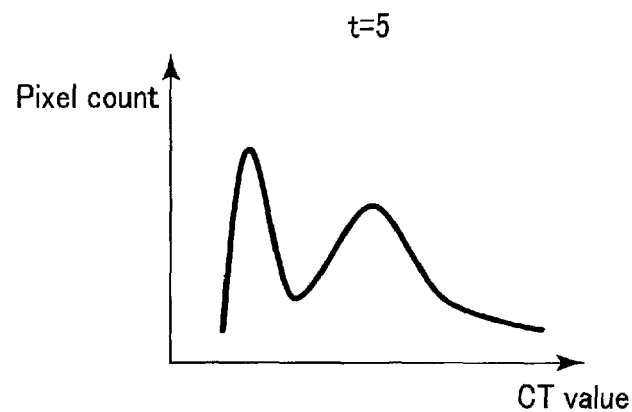
F I G. 4
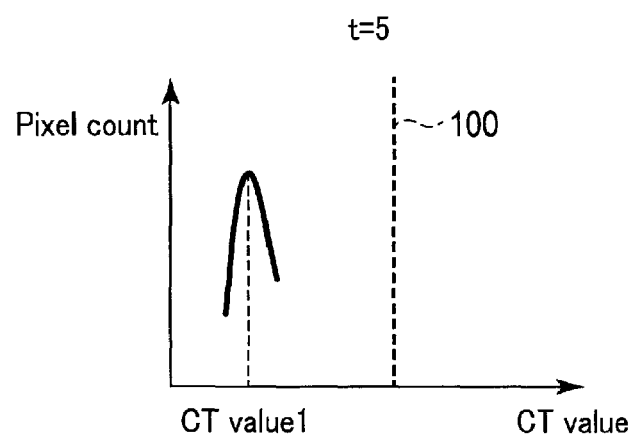
F I G. 5
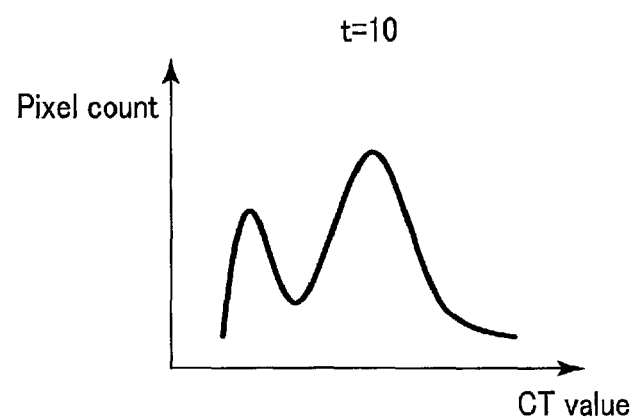
F I G. 6

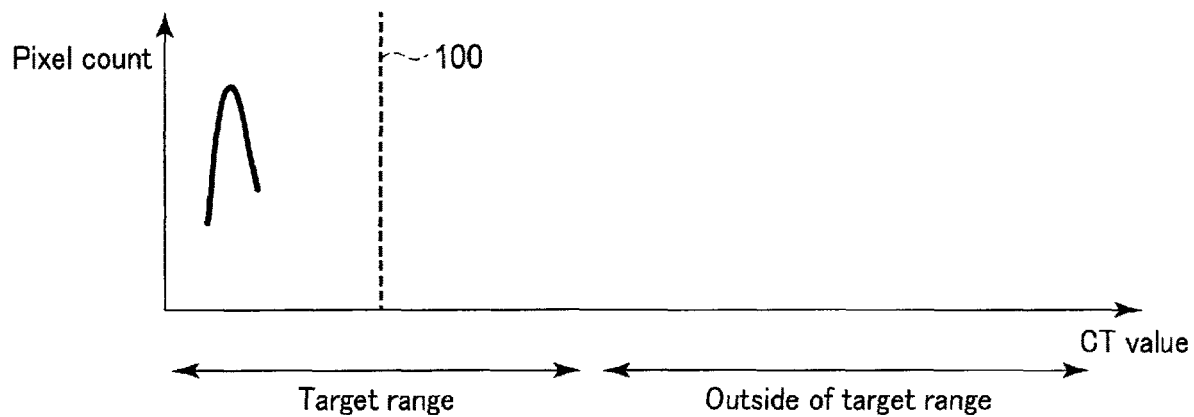
F I G. 10
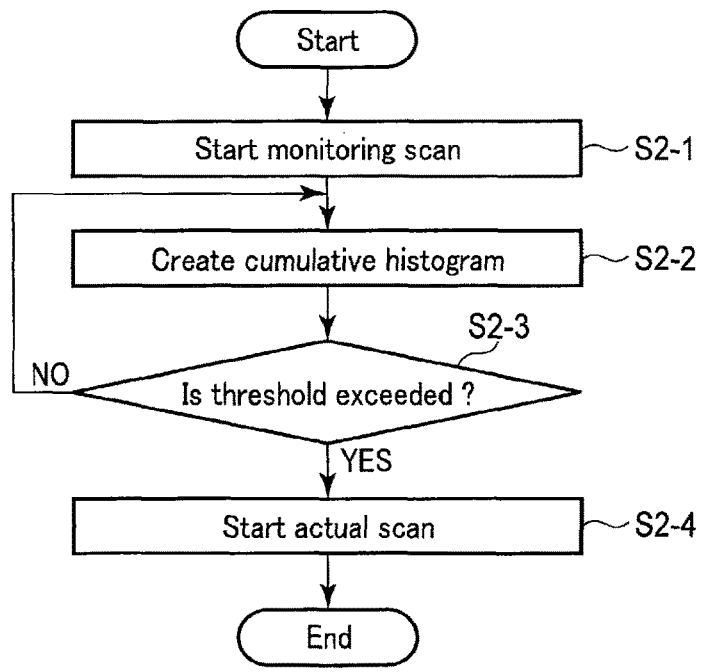
F I G. 11

X-RAY COMPUTED TOMOGRAPHY APPARATUS AND CONTRAST MEDIUM INFLOW AMOUNT DETECTION METHOD

CROSS-REFERENCE TO RELATED APPLICATIONS

This application is a Continuation Application of PCT application No. PCT/JP2014/068236, filed on Jul. 8, 2014, and is based upon and claims the benefit of priority from Japanese Patent Application No. 2013-142496, filed on Jul. 8, 2013, the entire contents of which are incorporated herein by reference.

FIELD

Embodiments described herein relate generally to an X-ray computed tomography apparatus and a contrast medium inflow amount detection method.

BACKGROUND

In general, an X-ray computed tomography apparatus (to be referred to as an X-ray CT apparatus hereinafter) is an apparatus capable of capturing a tomographic image of an object by scanning the object with X-rays.

In the X-ray CT apparatus, a contrast medium may be used to clearly depict pathogens and the like in a tomographic image. In imaging using the contrast medium (to be referred to as contrast medium imaging hereinafter), it is important to perform a scan (actual scan) when a contrast medium administered to an object flows into a slice of interest. Therefore, before the actual scan, a scan (monitoring scan) is performed with X-rays at a dose lower than that at the time of the actual scan. In this case, an imaging technician or the like can visually perceive the contrast medium concentration (contrast) of a region of interest of a tomographic image obtained by the monitoring scan. Thus, when the concentration becomes high to some extent, the actual scan can be started.

In recent years, a technique of automating a scan start timing has become widespread. In this technique, the CT values of a region of interest (for example, the cross section of a blood vessel in which an inflow of a contrast medium can be identified) extracted from a tomographic image (real-time image) obtained by a monitoring scan or the average value of the CT values is compared with a threshold. When the threshold is exceeded, a shift from the monitoring scan to an actual scan is performed.

BRIEF DESCRIPTION OF THE DRAWINGS

FIG. 1 is a block diagram showing the arrangement of an X-ray computed tomography apparatus according to the first embodiment.

FIG. 4 is a graph showing an example of a histogram for t=5.

FIG. 5 is a graph showing the difference between the histogram shown in FIG. 3 and that shown in FIG. 4.

FIG. 6 is a graph showing an example of a histogram for t=10.

FIG. 10 is a graph for explaining an arrangement of acquiring a difference only within a predetermined CT value range.

FIG. 11 is a flowchart illustrating a processing procedure when switching from a monitoring scan to an actual scan in an X-ray CT apparatus according to the second embodiment.

DETAILED DESCRIPTION

Figure 2:
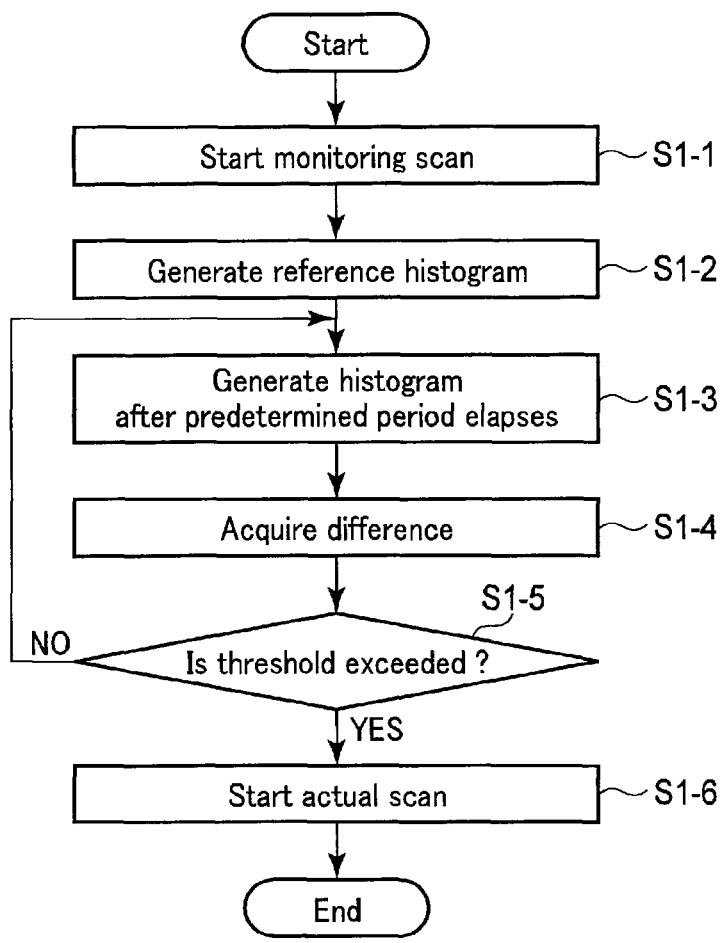
FIG. 2 is a flowchart illustrating a processing procedure when switching from a monitoring scan to an actual scan in the X-ray CT apparatus according to the first embodiment.

In general, according to an embodiment, an X-ray computed tomography apparatus that executes a monitoring scan for detecting an inflow amount of a contrast medium administered to an object and an actual scan under a scan condition different from that of the monitoring scan includes reconstruction circuitry and control circuitry. The reconstruction circuitry is configured to, at the time of the monitoring scan, based on an output of an X-ray detector for detecting X-rays having passed through the object, reconstruct a first image concerning the object at the time of administration of the contrast medium and a second image concerning the object after a predetermined period elapses since administration of the contrast medium. The control circuitry is configured to shift from the monitoring scan to the actual scan based on a change amount of a CT value obtained when the entire reconstructed first image is compared with the entire reconstructed second image.

The first embodiment will be described below with reference to the accompanying drawings.

First Embodiment

The arrangement of an X-ray computed tomography apparatus (to be referred to as an X-ray CT apparatus hereinafter) according to this embodiment will be explained with reference to FIG. 1.

The X-ray CT apparatus according to this embodiment has a function of executing a monitoring scan (prep scan) and an actual scan for an object to which a contrast medium is administered. Note that the monitoring scan indicates a scan that is performed with X-rays at a dose lower than that at the time of the actual scan to detect the inflow amount of the contrast medium administered to the object into an imaging portion. On the other hand, the actual scan indicates a scan that is performed under a scan condition different from that of the monitoring scan, and performed to obtain an image for diagnosing the object.

As shown in FIG. 1, the X-ray CT apparatus includes a gantry 10 and a console 20. The gantry 10 includes an X-ray generation device 11, a rotating frame 12, a rotating frame driving unit 13, an X-ray detector 14, a data acquisition system 15, and a transmission unit 16.

The X-ray generation device 11 generates X-rays to be emitted to an object P. The X-ray generation device 11 includes an X-ray tube 111, a high voltage generation unit 112, and an X-ray control unit 113.

The X-ray tube 111 includes, for example, a cathode and anode. A tube voltage is applied between the cathode and anode of the X-ray tube 111, and a filament current is supplied to the filament of the cathode of the X-ray tube 111. By applying the tube voltage and supplying the filament current, X-rays are generated from the anode of the X-ray tube 111. More specifically, upon receiving supply of the filament current, the filament of the cathode is heated to generate thermoelectrons. The generated thermoelectrons collide with the target of the anode due to the tube voltage applied between the filament of the cathode and the anode. When thermoelectrons collide with the target of the anode, X-rays are generated. Note that a tube current flows through the X-ray tube 111 due to thermoelectrons that collide with the target of the anode. The tube current is adjusted by the filament current. An X-ray dose at the time of a scan (imaging) by the X-ray CT apparatus is adjusted by adjusting the current time product that is the product of a tube current and an X-ray duration.

To generate X-rays from the X-ray tube 111, the high voltage generation unit 112 generates a tube voltage to be applied to the X-ray tube 111.

The X-ray control unit 113 controls generation of X-rays from the X-ray tube 111 by controlling the high voltage generation unit 112.

The rotating frame 12 is an annular or disc-like rotating frame that continuously rotates about the object P at high speed. This rotating frame 12 supports the X-ray tube 111 and X-ray detector 14 to be rotatable about the center axis (rotation axis) of the rotating frame 12. An FOV (Field Of View) is set in the opening of the rotating frame 12. The rotating frame 12 is connected to the rotating frame driving unit 13.

The rotating frame driving unit 13 rotates the rotating frame 12 at a predetermined angular velocity to rotate the X-ray tube 111 and X-ray detector 14 about the rotation axis. Note that the rotating frame driving unit 13 rotates the rotating frame 12 (X-ray tube 111 and X-ray detector 14) about a Z-axis that is defined as a rotation axis in FIG. 1.

A top support mechanism 121 is installed near the rotating frame 12. The top support mechanism 121 supports a top 122 to be movable along the Z-axis. The top support mechanism 121 supports the top 122 so that the major axis of the top 122 becomes parallel to the Z-axis. The object P is placed on the top 122. By power generated by a motor (not shown), the top support mechanism 121 moves the top 122 along the Z-axis direction.

The X-ray detector 14 detects X-rays (X-rays having passed through the object P) generated from the X-ray tube 111. The X-ray detector 14 includes a plurality of detection elements arrayed two-dimensionally. For example, the plurality of detection elements are arrayed along an arc centered on the rotation axis Z of the rotating frame 12. The detection element array direction along the arc is called a channel direction. A plurality of rows of detection elements are arrayed in the column direction along the rotation axis Z. Each detection element detects X-rays generated from the X-ray tube 111, and generates an electrical signal corresponding to the intensity of the detected X-rays. The generated electrical signal is supplied to the data acquisition system (DAS) 15.

The data acquisition system 15 acquires electrical signals for respective views via the X-ray detector 14. A view corresponds to a rotation angle of the rotating frame 12 about the rotation axis Z. In terms of signal processing, a view corresponds to a sampling point of data during rotation of the rotating frame 12. The data acquisition system 15 converts the acquired analog electrical signal into digital data. Note that the digital data is called raw data. A non-contact transmission unit 16 supplies the raw data to the console 20 for each predetermined view.

The console 20 includes a preprocessing unit 21, a reconstruction unit 22, a display unit 23, an operation unit 24, a storage unit 25, and a system control unit 26.

The preprocessing unit 21 executes preprocessing such as logarithmic transformation and sensitivity correction for the raw data supplied from the data acquisition system 15 via the transmission unit 16. The data having undergone the preprocessing is called projection data.

Based on the data (projection data) having undergone the preprocessing by the preprocessing unit 21, the reconstruction unit 22 reconstructs an image (data) concerning the object P.

The display unit 23 displays the image data reconstructed by the reconstruction unit 22 on, for example, a display device. As the display device, for example, a CRT display, a liquid crystal display, an organic EL display, a plasma display, or the like can be used, as needed.

The operation unit 24 accepts various instructions and information inputs from an operator via an input device. Assume that the operator can set, for example, a monitoring scan condition and an actual scan condition in the X-ray CT apparatus via the operation unit 24. Note that a keyboard, a mouse, a switch, and the like can be used as the input device.

The storage unit 25 stores the above-described raw data, projection data, image data, and the like. The storage unit 25 also stores a control program of the X-ray CT apparatus according to this embodiment.

The system control unit 26 functions as the main unit of the X-ray CT apparatus. More specifically, the system control unit 26 reads out the control program stored in the storage unit 25, loads it on a memory, and controls the respective units of the X-ray CT apparatus in accordance with the expanded control program.

While the above-described monitoring scan is executed, the system control unit 26 detects the inflow amount of the contrast medium administered to the object into the imaging portion, and switches from the monitoring scan to the actual scan. More specifically, the system control unit 26 shifts from the monitoring scan to the actual scan based on the change amount of a CT value (a value corresponding to each pixel forming an image) obtained when the entire image (first image) reconstructed by the reconstruction unit 22 at the time of the monitoring scan and concerning the object P at the time of administration of the contrast medium is compared with the entire image (second image) concerning the object P after a predetermined period elapses since administration of the contrast medium.

The operation of the X-ray CT apparatus according to this embodiment will be described with reference to a flowchart shown in FIG. 2. A processing procedure when switching from the monitoring scan to the actual scan in the X-ray CT apparatus will be mainly explained.

The monitoring scan is a scan performed for the purpose of detecting the inflow amount (contrast medium concentration) of the contrast medium administered to the object into the imaging portion in order to perform the actual scan at an appropriate timing in contrast medium imaging.

The system control unit 26 included in the console 20 starts the monitoring scan by controlling the respective units of the X-ray CT apparatus (step S1-1). In this monitoring scan, a scan is executed with X-rays at a dose lower than that at the time of the actual scan, and real-time images including an image concerning the object P at the time of administration of the contrast medium and an image concerting the object P obtained for every predetermined period after administration of the contrast medium are generated (reconstructed). Note that a real-time image generated in the monitoring scan includes the imaging portion as the target of the actual scan.

Note that a monitoring scan condition and an actual scan condition are preset before the start of the monitoring scan.

Based on the image reconstructed by the monitoring scan and concerning the object P at the time of administration of the contrast medium, the system control unit 26 generates a reference histogram (first histogram) of the CT values of the entire image (step S1-2). This reference histogram represents a pixel count corresponding to each CT value of the entire image concerning the object P at the time of administration of the contrast medium.

Based on the image reconstructed by the monitoring scan and concerning the object P after the predetermined period elapses since administration of the contrast medium, the system control unit 26 generates a histogram (second histogram) of the CT values of the entire image (step S1-3). The histogram generated in step S1-3 will be referred to as a comparison target histogram, for the sake of convenience.

The system control unit 26 compares the reference histogram acquired in step S1-2 with the comparison target histogram acquired in step S1-3 to acquire the difference between the reference histogram and the comparison target histogram (step S1-4). Note that the difference acquired by the system control unit 26 represents the CT value in the comparison target histogram, for which the pixel count increases with respect to the reference histogram.

The system control unit 26 determines whether the CT value represented by the acquired difference exceeds a predetermined value (to be referred to as a threshold hereinafter) (step S1-5).

If it is determined that the CT value represented by the difference does not exceed the threshold (NO in step S1-5), the process returns to step S1-3 to repeat the processing.

On the other hand, if it is determined that the CT value represented by the difference exceeds the threshold, the system control unit 26 stops the monitoring scan, and switches to the actual scan. This starts the actual scan in the X-ray CT apparatus (step S1-6).

As described above, according to this embodiment, it is possible to detect the inflow amount of the contrast medium by paying attention to the difference between the reference histogram and the comparison target histogram obtained for every predetermined period (that is, the change amount of the histogram for each time).

The operation when switching from the monitoring scan to the actual scan will now be described in detail with reference to FIGS. 3, 4, 5, 6, 7, 8, and 9. Note that t represents an elapsed time after administration of the contrast medium in the following description.

Figure 3:
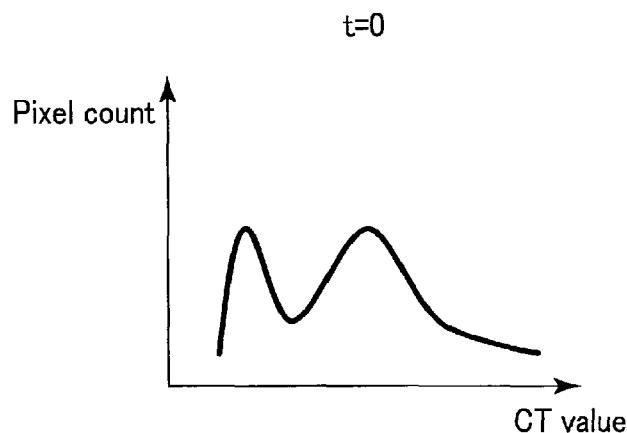
FIG. 3 is a graph showing an example of a histogram for t=0.

FIG. 3 shows an example of a histogram (that is, the reference histogram at the time of administration of the contrast medium) for t=0. FIG. 4 shows an example of a histogram (comparison target histogram) for t=5. FIG. 5 shows the difference between the histogram shown in FIG. 3 for t=0 and the histogram shown in FIG. 4 for t=5.

With reference to FIG. 5, in the difference between the histogram shown in FIG. 3 for t=0 and the histogram shown in FIG. 4 for t=5, a pixel count corresponding to a CT value 1 is largest. That is, the CT value in the histogram shown in FIG. 4 for t=5, for which the pixel count increases most with respect to the histogram shown in FIG. 3 for t=0, is the CT value 1. Note that the increase in pixel count corresponding to the CT value 1 is caused by an inflow of a large amount of contrast medium into the imaging portion for t=5, as compared with an amount of contrast medium for t=0.

In this case, the CT value 1 is compared with a threshold 100 (the CT value set as the threshold 100). However, as shown in FIG. 5, since the CT value 1 does not exceed the threshold 100, it is determined that the inflow amount (contrast medium concentration) of the contrast medium administered to the object into the imaging portion for t=5 is insufficient, and thus the actual scan is not started.

Figure 7:
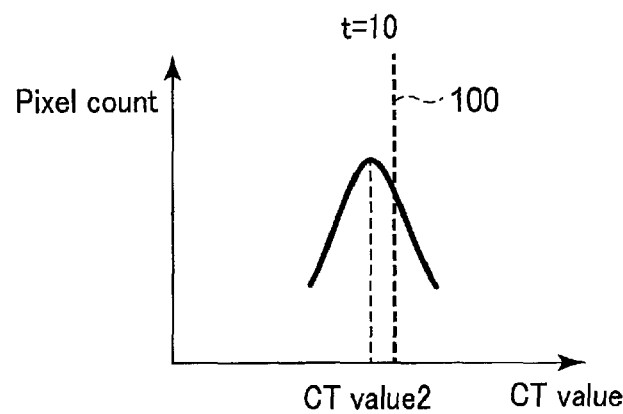
FIG. 7 is a graph showing the difference between the histogram shown in FIG. 3 and that shown in FIG. 6.

FIG. 6 shows an example of a histogram for t=10. FIG. 7 shows the difference between the histogram shown in FIG. 3 for t=0 and the histogram shown in FIG. 6 for t=10.

With reference to FIG. 7, in the difference between the histogram shown in FIG. 3 for t=0 and the histogram shown in FIG. 6 for t=10, a pixel count corresponding to a CT value 2 is largest. That is, the CT value in the histogram shown in FIG. 6 for t=10, for which the pixel count increases most with respect to the histogram shown in FIG. 3 for t=0, is the CT value 2. The increase in pixel count corresponding to the CT value 2 indicates that a large amount of contrast medium flows into the imaging portion for t=10, as compared with an amount of contrast medium for t=0. The reason why the CT value 2 is larger than the CT value 1 is that the inflow amount of the contrast medium into the imaging portion for t=10 is larger than that for t=5.

In this case, the CT value 2 is compared with the threshold 100. However, as shown in FIG. 7, since the CT value 2 does not exceed the threshold 100, it is determined that the inflow amount of the contrast medium administered to the object into the imaging portion for t=10 is insufficient, and thus the actual scan is not started.

Figure 8:
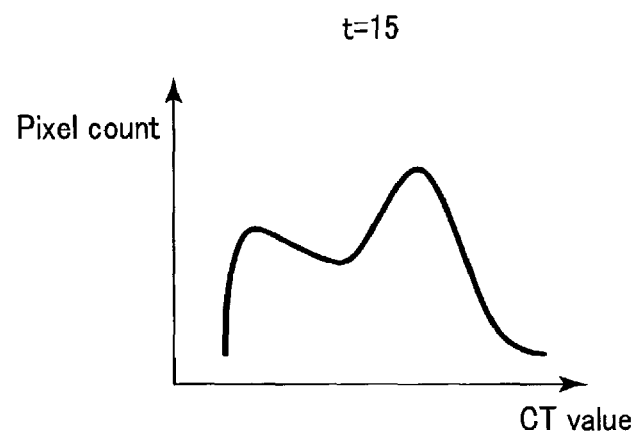
FIG. 8 is a graph showing an example of a histogram for t=15.
Figure 9:
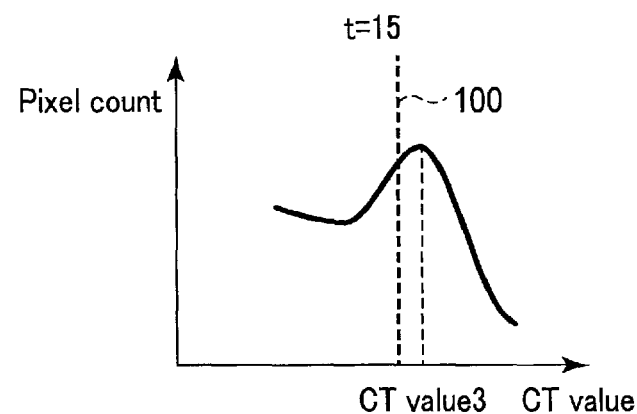
FIG. 9 is a graph showing the difference between the histogram shown in FIG. 3 and that shown in FIG. 8.

FIG. 8 shows an example of a histogram for t=15. FIG. 9 shows the difference between the histogram shown in FIG. 3 for t=0 and the histogram shown in FIG. 8 for t=15.

With reference to FIG. 9, in the difference between the histogram shown in FIG. 3 for t=0 and the histogram shown in FIG. 8 for t=15, a pixel count corresponding to a CT value 3 is largest. That is, the CT value in the histogram shown in FIG. 8 for t=15, for which the pixel count increases most with respect to the histogram shown in FIG. 3 for t=0, is the CT value 3. The increase in pixel count corresponding to the CT value 3 indicates that a large amount of contrast medium flows into the imaging portion for t=15, as compared with an amount of contrast medium for t=0. The reason why the CT value 3 is larger than the CT values 1 and 2 is that the inflow amount of the contrast medium into the imaging portion for t=15 is larger than those for t=5 and t=10.

In this case, the CT value 3 is compared with the threshold 100. However, as shown in FIG. 9, since the CT value 3 exceeds the threshold 100, it is determined that the inflow amount of the contrast medium administered to the object into the imaging portion for t=15 is sufficient (that is, the contrast medium has flowed into the imaging portion), and the monitoring scan is switched to the actual scan (that is, the actual scan is started).

Note that the above description assumes that the CT value for which the corresponding pixel count is largest in the difference is compared with the threshold but the average value of the CT values in the difference or the like may be compared with the threshold.

As described above, according to this embodiment, with the arrangement of shifting from the monitoring scan to the actual scan based on the change amount of the CT value between the entire image reconstructed by the monitoring scan and concerning the object P at the time of administration of the contrast medium and the entire image concerning the object P after the predetermined period elapses since administration of the contrast medium (that is, based on the difference between the histogram for t=0 and that for t=5, t=10, or t=15), it is possible to appropriately detect (grasp) the inflow amount of the contrast medium administered to the object into the imaging portion without setting a region of interest, thereby starting the actual scan. That is, according to this embodiment, since the inflow amount of the contrast medium is detected based on the CT values of the entire image reconstructed by the monitoring scan instead of the CT values of a region of interest, it is possible to reduce the exposure dose of the object without needing a registration scan for setting a region of interest.

According to this embodiment, since it is not necessary to perform an operation of setting a region of interest at the time of the monitoring scan (that is, an operation is completely automated), it is possible to improve the workflow/throughput, and also start the actual scan at an appropriate timing without any influence of the technique and experience of an operator or the like.

According to this embodiment, since the CT values of the entire image reconstructed by the monitoring scan are used, the influence of noise and the like is hardly exerted, and even if the position of the imaging portion on the image shifts by body motion at the time of the monitoring scan, it is possible to start the actual scan at an appropriate timing without any influence. Therefore, in this embodiment, it is possible to achieve high robustness.

As described above, according to this embodiment, it is possible to detect the inflow amount of the contrast medium without any influence in the case of small body motion. However, for example, if the object largely moves in the Z-axis direction, the difference between histograms largely changes, and thus it is possible to detect such body motion by, for example, setting an allowable range for the difference. If such body motion is detected, a notification that it is impossible to start the actual scan is sent or the actual scan is not started unless an instruction is received from an operator.

Note that a possible CT value range when the contrast medium flows into the imaging portion is determined to some extent. Therefore, according to this embodiment, the apparatus can be configured to acquire the difference only within a predetermined CT value range. That is, as shown in FIG. 10, it is possible to improve the detection accuracy of the inflow amount of the contrast medium by excluding, from a difference target range, a CT value range assumed not to be related with the inflow of the contrast medium (for example, a range largely deviating from the threshold).

Second Embodiment

The second embodiment will be described next.

In the first embodiment, the system control unit 26 acquires the difference between the reference histogram and the comparison target histogram by comparing the reference histogram with the comparison target histogram, and determines whether the CT value represented by the difference exceeds the predetermined threshold. If it is determined that the CT value represented by the difference exceeds the threshold, the system control unit 26 stops the monitoring scan, and switches to the actual scan, thereby starting the actual scan in the X-ray CT apparatus.

In the second embodiment, with respect to a result of accumulating the time-series differences between histograms, it is controlled to stop a monitoring scan based on a pixel count corresponding to a CT value within a predetermined range, and switch to an actual scan.

The operation of an X-ray CT apparatus according to this embodiment will be described with reference to a flowchart shown in FIG. 11. A processing procedure when switching from the monitoring scan to the actual scan in the X-ray CT apparatus will be mainly explained.

The monitoring scan is a scan performed for the purpose of detecting the inflow amount (contrast medium concentration) of a contrast medium administered to an object into an imaging portion in order to perform the actual scan at an appropriate timing in contrast medium imaging.

A system control unit 26 included in a console 20 starts the monitoring scan by controlling the respective units of the X-ray CT apparatus (step S2-1). In this monitoring scan, a scan is executed with X-rays at a dose lower than that at the time of the actual scan, and real-time images including an image concerning an object P at the time of administration of the contrast medium and an image concerning the object P obtained for every predetermined period after administration of the contrast medium are generated (reconstructed). Note that a real-time image generated in the monitoring scan includes the imaging portion as the target of the actual scan.

Note that a monitoring scan condition and an actual scan condition are preset before the start of the monitoring scan.

Based on the images reconstructed by the monitoring scan and concerning the object P after administration of the contrast medium, the system control unit 26 creates histograms of the CT values of the entire images, and obtains time-series differences. For example, the difference value between the histogram for t=0 and the histogram for t=1 and the difference value between the histogram for t=1 and the histogram for t=2 are created. Then, these difference values are accumulated to create a cumulative histogram (step S2-2).

The system control unit 26 determines whether the maximum value of pixel values corresponding to CT values within the predetermined range represented by the acquired cumulative histogram, that is, the peak value of the pixel values corresponding to the CT values' within the predetermined range exceeds a predetermined value (to be referred to as a threshold hereinafter) (step S2-3).

If it is determined that the peak value does not exceed the threshold (NO in step S2-3), the process returns to step S2-2 to repeat the processing.

On the other hand, if it is determined that the peak value exceeds the threshold, the system control unit 26 stops the monitoring scan, and switches to the actual scan. This starts the actual scan in the X-ray CT apparatus (step S2-4).

Note that the system control unit 26 stops the monitoring scan by comparing the peak value of the pixel values corresponding to the CT values within the predetermined range with the threshold, and switches to the actual scan, as described above. However, the embodiment is not limited to this.

For example, the system control unit 26 may calculate the sum or average value of the pixel values corresponding to the CT values within the predetermined range, and compares the sum or average value with a corresponding threshold, thereby stopping the monitoring scan and switching to the actual scan.

As described above, according to this embodiment, it is possible to detect the inflow amount of the contrast medium by paying attention to changes in pixel values corresponding to the CT values within the predetermined range in the result of accumulating the time-series differences between the histograms.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

The invention claimed is:

1. An X-ray computed tomography (CT) apparatus comprising:
   an imaging unit that executes an actual scan, and a monitoring scan for imaging a range including an imaging portion of the actual scan before start of the actual scan;
   reconstruction circuitry configured to, at a time of the monitoring scan not setting a region of interest, based on an output of an X-ray detector for detecting X-rays having passed through an object, reconstruct a first image concerning object at a time of administration of a contrast medium and a second image concerning the object after a predetermined period elapses since administration of the contrast medium; and
   control circuitry configured to
      generate a first histogram representing a pixel count corresponding to each CT value in the entirety of the first image,
      generate, for every predetermined period, a second histogram representing a pixel count corresponding to each CT value in the entirety of the second image, sequentially acquire a difference histogram corresponding to a difference between the first histogram and the second histogram for which a pixel count increases with respect to the first histogram, and sequentially acquire a CT value corresponding to a largest pixel count in the difference histogram, and
      control at least one of stopping the monitoring scan or starting the actual scan when the acquired CT value exceeds a predetermined threshold,
   the imaging unit executing no registration scan for setting the region of interest.

2. The X-ray computed tomography apparatus according to claim 1, wherein the control circuitry is further configured to acquire the CT value corresponding to the largest pixel count in the difference histogram within a predetermined CT value range.

3. An X-ray computed tomography (CT) apparatus, comprising:
   an imaging unit that executes a monitoring scan for detecting an inflow amount of a contrast medium administered to an object and, after the monitoring scan, an actual scan under a scan condition different from that of the monitoring scan;
   reconstruction circuitry configured to, at a time of the monitoring scan not setting a region of interest, based on an output of an X-ray detector for detecting X-rays having passed through the object, reconstruct a first image concerning the object at a time of administration of the contrast medium and a second image concerning the object after a predetermined period elapses since administration of the contrast medium; and
   control circuitry configured to generate a first histogram representing a pixel count corresponding to each CT value in the entirety of the first image, sequentially generate a second histogram and a third histogram each representing a pixel count corresponding to each CT value in the entirety of the second image, and shift from the monitoring scan to the actual scan based on whether a peak value of a pixel value corresponding to a predetermined CT value range exceeds a threshold in a cumulative histogram obtained by accumulating a difference between the first histogram at a first point of time and the second histogram at a second point of time after the first point of time, and a difference between the second histogram at the second point of time and the third histogram at a third point of time after the second point of time, within the predetermined CT value range,
   the imaging unit executing no registration scan for setting the region of interest.

* * * * *